United States Patent
Chapus

(10) Patent No.: US 9,260,385 B2
(45) Date of Patent: Feb. 16, 2016

(54) PROCESS FOR THE PRODUCTION OF SURFACTANTS FROM RENEWABLE MATERIALS, COMPRISING A STEP FOR HYDROTREATMENT AND A STEP FOR TRANSFORMING PARAFFINS INTO SURFACTANTS

(71) Applicant: IFP ENERGIES NOUVELLES, Rueil-Malmaison Cedex (FR)

(72) Inventor: Thierry Chapus, Lyons (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 0 days.

(21) Appl. No.: 14/409,654

(22) PCT Filed: Apr. 18, 2013

(86) PCT No.: PCT/FR2013/050850
§ 371 (c)(1),
(2) Date: Dec. 19, 2014

(87) PCT Pub. No.: WO2013/190193
PCT Pub. Date: Dec. 27, 2013

(65) Prior Publication Data
US 2015/0166473 A1  Jun. 18, 2015

(30) Foreign Application Priority Data

Jun. 21, 2012 (FR) ..................... 12 01760

(51) Int. Cl.
C07C 303/04 (2006.01)
C10G 29/20 (2006.01)
(Continued)

(52) U.S. Cl.
CPC ............. *C07C 303/04* (2013.01); *B01J 8/0453* (2013.01); *B01J 8/0492* (2013.01); *C07C 1/2076* (2013.01); *C07C 1/2078* (2013.01); *C07C 1/24* (2013.01); *C07C 2/66* (2013.01); *C07C 2/72* (2013.01); *C10G 3/50* (2013.01); *C10G 3/60* (2013.01); *C10G 29/205* (2013.01); *C10G 29/28* (2013.01); *C10G 45/72* (2013.01); *B01J 2208/00283* (2013.01); *C07C 2521/04* (2013.01);
(Continued)

(58) Field of Classification Search
None
See application file for complete search history.

(56) References Cited

U.S. PATENT DOCUMENTS 8,197,559 B2   6/2012 Abe et al.
2007/0281875 A1 * 12/2007 Scheibel et al. .............. 510/101

(Continued)

FOREIGN PATENT DOCUMENTS

EP   2226375 A1   9/2010
EP   2428548   *   3/2012
(Continued)

OTHER PUBLICATIONS

International Search Report dated Jun. 19, 2013 issued in corresponding PCT/FR2013/050850 application (pp. 1-2).

*Primary Examiner* — Karl J Puttlitz
(74) *Attorney, Agent, or Firm* — Millen, White, Zelano and Branigan, P.C.

(57) ABSTRACT

A process for the production of surfactant compounds from a feed obtained from renewable sources, comprising hydrotreatment of feed in a fixed bed reactor having a plurality of catalytic zones disposed in series containing a hydrotreatment catalyst. The feed is injected in a staggered manner and injected in increasing proportions in order to produce an effluent containing at least hydrocarbon compounds containing linear paraffins.

15 Claims, 2 Drawing Sheets

(51) Int. Cl.
*C10G 29/28* (2006.01)
*C10G 45/72* (2006.01)
*C10G 3/00* (2006.01)
*B01J 8/04* (2006.01)
*C07C 1/207* (2006.01)
*C07C 1/24* (2006.01)
*C07C 2/66* (2006.01)
*C07C 2/72* (2006.01)

(52) U.S. Cl.
CPC ......... *C07C2523/28* (2013.01); *C07C 2523/30* (2013.01); *C07C 2523/75* (2013.01); *C07C 2523/755* (2013.01); *C10G 2300/1011* (2013.01)

(56) References Cited

U.S. PATENT DOCUMENTS

2010/0242349 A1\* 9/2010 Abe et al. ............... 44/398
2013/0255138 A1 10/2013 Mayeur et al.

FOREIGN PATENT DOCUMENTS

| EP | 2428548 | A1 | 3/2012 |
| FR | 2967687 | A1 | 5/2012 |
| WO | 2010100565 | \* | 9/2010 |

\* cited by examiner

PROCESS FOR THE PRODUCTION OF SURFACTANTS FROM RENEWABLE MATERIALS, COMPRISING A STEP FOR HYDROTREATMENT AND A STEP FOR TRANSFORMING PARAFFINS INTO SURFACTANTS

The invention relates to a process for the production of surfactant compounds from a feed obtained from renewable sources such as oils and fats of vegetable or animal origin, comprising a step for hydrotreatment of said feed to produce paraffinic hydrocarbons, in particular n-paraffinic, and a step for transformation of said paraffinic hydrocarbons into surfactants which can in particular be used as detergents.

The current international context is marked firstly by the need to discover substitutes for oil products for fuel applications and also for chemical product manufacturing applications. Chemical products which can be cited include surfactants ("surface active agents") which are characterized by their capacity to reduce the surface tension between two surfaces. Said surfactants are amphiphilic molecules, i.e. having two portions with different polarities, one lipophilic and apolar, the other hydrophilic, i.e. miscible with water, and polar. The remarkable properties of surfactants explain their use in a large number of applications, as detergents, solubilizing agents, foaming agents, wetting agents, dispersing agents or indeed emulsifiers.

In this context, research into novel feeds obtained from renewable sources constitutes a challenge of ever-increasing importance. Examples of such feeds which may be cited are vegetable oils (food quality or otherwise) or those obtained from algae and animal fats.

Feeds of this type are principally composed of triglycerides and/or free fatty acids and/or esters, these molecules comprising hydrocarbon chains of fatty acids containing 4 to 25 carbon atoms, and a number of unsaturated bonds, generally in the range 0 to 3, with higher values for oils from algae, for example. The renewable feeds also contain impurities such as nitrogen-containing compounds and metals present in the form of phospholipids containing elements such as phosphorus, calcium, magnesium, potassium or sodium.

The hydrocarbon chains which constitute said feeds are essentially linear and their length in terms of the number of carbon atoms is generally in the range 4 to 25.

Thus, it would be of interest to transform such renewable feeds. One possible approach is the catalytic transformation of said feeds into deoxygenated paraffinic hydrocarbon compounds in the presence of hydrogen, and in particular by hydrotreatment.

During hydrotreatment, the reactions undergone by said feed containing triglycerides and/or fatty acids and/or esters are as follows:
  the reaction for hydrogenation of the unsaturated bonds of the hydrocarbon chains of the triglycerides, fatty acids and esters;
  reactions for deoxygenation in accordance with two possible reaction pathways:
    hydrodeoxygenation (HDO) leading to the formation of water by consumption of hydrogen and to the formation of hydrocarbons with a carbon number ($C_n$) equal to that of the initial fatty acid chains;
    decarboxylation/decarbonylation, leading to the formation of oxides of carbon (carbon monoxide and dioxide: CO and $CO_2$) and to the formation of hydrocarbons containing one fewer carbon atoms ($C_{n-1}$) than the initial fatty acid chains.

The hydrogenation of the unsaturated bonds of hydrocarbon chains (carbon-carbon double bonds) is highly exothermic and the increase in temperature caused by the release of heat may result in temperatures where the part played by decarboxylation reactions becomes more favoured. Hydrodeoxygenation reactions, including decarboxylation reactions, are also exothermic reactions.

A strict control of the temperature in the hydrotreatment section is necessary, since too high a temperature can also suffer from the disadvantage of favouring unwanted secondary reactions such as polymerization, cracking, coke deposition and catalyst deactivation. The polymerization reactions may result in degradation of the feed before it is transformed in accordance with the desired pathway. Cracking reactions have the disadvantage of degrading the yield for the desired transformation.

Furthermore, the paraffinic hydrocarbons produced by treating said feeds with hydrogen are exclusively linear paraffins (n-paraffins), i.e. not branched. As a consequence, it is possible to transform them:
  either into long chain paraffin sulphonates by sulphonation;
  or into alkylated aromatic hydrocarbons (such as "Linear Alkyl Benzenes") by means of an alkylation reaction between the linear paraffins and aromatic hydrocarbons selected from benzene, toluene or indeed xylenes.

Compounds such as long chain paraffin sulphonates or alkylated aromatic hydrocarbons have advantageous surfactant properties, meaning that they can be used as bases for detergent products.

PRIOR ART

Patent application US 2007/0281875 proposes a process for the conversion of natural oils and fats comprising the following steps: a/ conversion, by elimination of oxygen, to produce paraffins and olefins by decarboxylation using an acid catalyst primarily comprising a zeolite; b/functionalization of the paraffins and olefins produced in step a/ by the OXO reaction in order to produce alcohols, or by alkylation by aromatic compounds of the benzene or toluene type using an alkylation catalyst; and c/ sulphonation or alkoxylation of the alkylbenzene type compounds produced during the preceding step in order to produce compounds forming part of the detergent composition.

Patent application US 2007/0281875 does not mention any strict control of the temperature in the first step, the critical element in said first step being the use of an activated acid catalyst, in particular the use of a zeolite.

The Applicant has demonstrated that a specific combination of operating conditions during the first hydrotreatment step consisting of transforming, while favouring the decarboxylation pathway, a feed obtained from renewable sources into hydrocarbon compounds constituted by linear paraffins, followed by a second step for transformation of the linear paraffins produced, means that surfactant compounds can be produced which, due to their interesting properties as solubilizing agents, have applications in particular as detergents, liquid soaps, emulsifiers or dispersing agents.

In particular, the step for transformation of the linear paraffins produced during the first step advantageously consists of either a/ a reaction for alkylation of the linear paraffins with aromatic hydrocarbons selected from benzene, toluene, xylenes or mixtures of such aromatic hydrocarbons into alkylated aromatic hydrocarbons; or b/ sulphonation of the linear paraffins, in order to produce alkane sulphonates, said alkylated aromatic hydrocarbons and said alkane sulphonates being surfactants.

AIM OF THE INVENTION

The aim of the present invention is thus to propose a process for the production of surfactant compounds from feeds of renewable origin containing lipids, triglycerides and/or fatty acids and/or esters.

Thus, the present invention concerns a process for the production of surfactant compounds from a feed obtained from renewable sources, comprising at least the following steps:

a) a step for hydrotreatment of said feed in order to produce an effluent containing at least hydrocarbon compounds constituted by linear paraffins, in the presence of hydrogen in excess of the theoretical hydrogen consumption and under hydrotreatment conditions, in a fixed bed reactor having a plurality of catalytic zones disposed in series and comprising a hydrotreatment catalyst, in which:

i) the total flow of feed F is divided into a certain number of different part flows, F1 to Fn, equal to the number of catalytic zones n in the reactor, the first part flow F1 is injected into the first catalytic zone, the second part flow F2 is injected into the second catalytic zone and so on, if n is greater than 2, the various part flows being injected into the successive catalytic zones in increasing proportions such that F1/F is less than or equal to F2/F, which itself is less than or equal to F3/F and so on until F(n−1)/F is less than or equal to Fn/F, the temperature of the flow injected into the inlet to the first catalytic zone Z1 comprising the part flow of the feed F1 mixed with the hydrogen-rich flow H1 entering the zone Z1 and with a liquid recycle R, (F1+R+H1), being greater than 250° C. and the temperature of the flows at the inlet to the subsequent zones Z2 to Zn being greater than 300° C.;

ii) said effluent containing at least the hydrocarbon compounds constituted by linear paraffins undergoes at least one separation step in order to separate a gaseous fraction containing hydrogen, CO, $CO_2$, $H_2S$, water and light gases and a liquid hydrocarbon fraction constituted by linear paraffins;

iii) at least a portion R of said liquid hydrocarbon fraction constituted by linear paraffins is recycled to the first catalytic zone Z1 such that the weight ratio between the flow for said recycle R and the part flow F1 introduced into the first catalytic zone Z1, R/F1, is 8 or more; b) a step for transforming at least a portion of said liquid hydrocarbon fraction constituted by linear paraffins obtained from step a) into surfactant compounds.

Introducing the feed in increasing proportions coupled with a large recycle to the first zone and the temperatures of the flows at the inlet to the various specific catalytic hydrotreatment zones means that, by using a rising temperature profile, a sufficiently hot zone can be produced at the end of the catalytic zone to favour the decarboxylation reactions over the hydrodeoxygenation reactions. Furthermore, in the case in which the initial feed comprises triglycerides and/or free fatty acids and/or esters with hydrocarbon chains containing more than 17 carbon atoms, step a) of the process of the present invention can be used to maximize the proportion of hydrocarbons of the linear paraffin type containing at most 17 carbon atoms.

Further, staggered injection of the feed, consisting of introducing increasing proportions of fresh feed into the hydrotreatment reaction zones, means that the change in temperatures in each catalytic zone can be managed as efficiently as possible.

Another advantage of the reaction resides in the fact that the temperatures of the flows at the inlet to the various catalytic hydrotreatment zones are such that any degradation of said feed of renewable origin by polymerization or cracking before it is transformed is avoided.

DETAILED DESCRIPTION OF THE INVENTION

Figure 1:
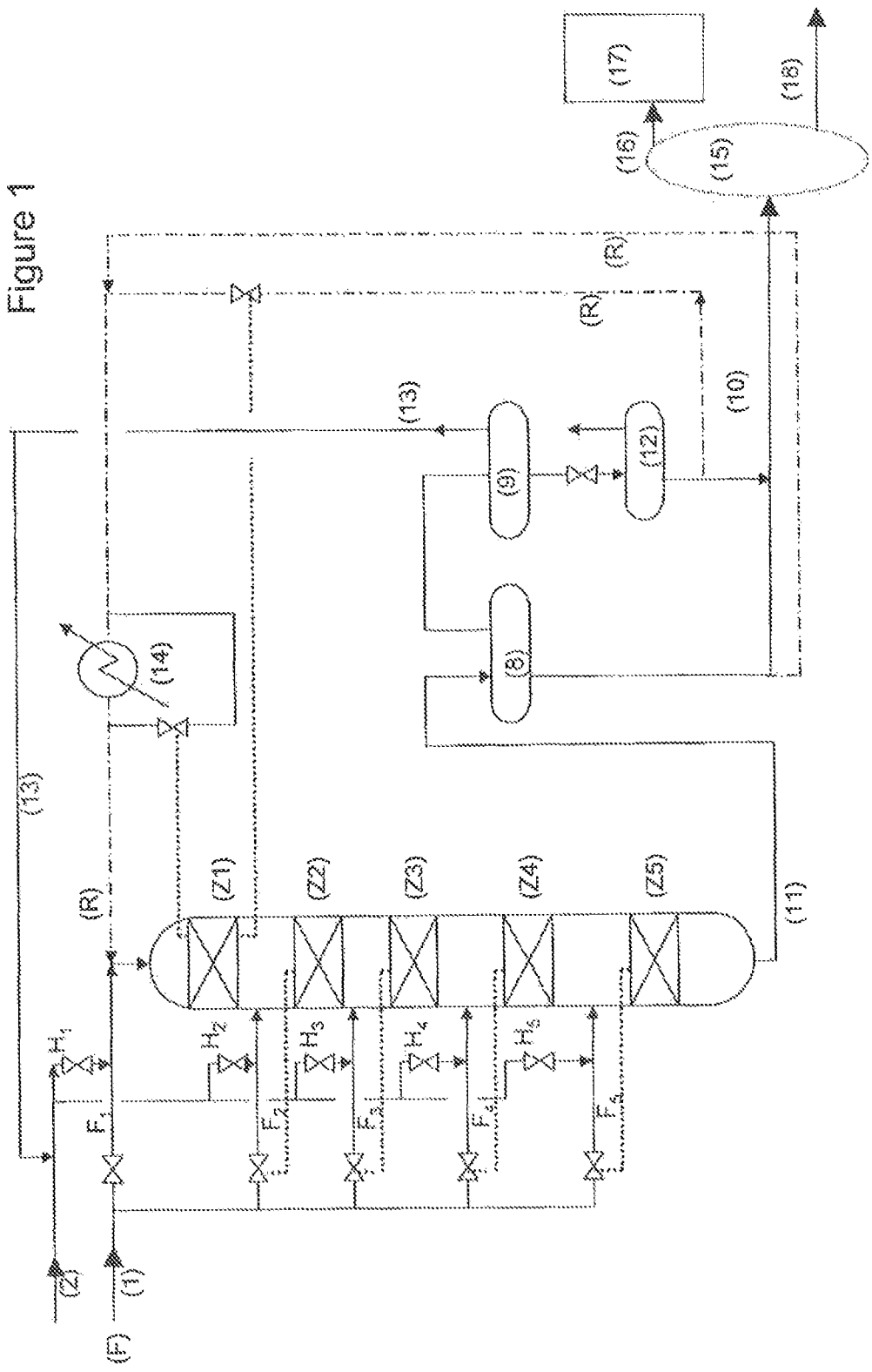
FIG. 1 is a schematic of a process in accordance with the invention.

The feeds obtained from renewable sources treated in the process of the present invention are selected from oils and fats of vegetable or animal origin, or mixtures of feeds of this type, containing triglycerides and/or free fatty acids and/or esters.

Said feeds are generally characterized by a high molar mass (usually greater than 800 g/mole) and the fatty acid chains of which they are composed contain in the range 4 to 24 carbon atoms and generally have in the range 0 to 3 unsaturated bonds per chain, with higher values which may be obtained for certain specific feeds. Examples of the feeds which may be treated in the process of the present invention which may be cited are from the following non-exhaustive list: vegetable oils such as rapeseed, jatropha, soya, palm, sunflower, olive, coprah, camelina, fish oils or heterotrophic or autotrophic algal oils, or animal fats such as beef suet, or indeed residues from the papermaking industry (such as tall oil), or mixtures of these various feeds. The various part flows of feed are advantageously identical or different in nature. One advantage of the process of the invention consists in its great flexibility, depending on the origin of the feed. Feeds which differ substantially from one to another, in particular in their varying degrees of unsaturation of the hydrocarbon chains, can be completely converted as regards the elimination of oxygen, while producing exclusively linear paraffinic hydrocarbons at the end of this hydrotreatment step a).

All of these feeds contain large quantities of oxygen as well as sulphur-containing compounds in highly varying amounts depending on the origin of the feeds, but also nitrogen-containing compounds, and metals such as phosphorus, calcium, magnesium, potassium or sodium. The quantity of metals may be up to 2500 ppm. The quantities of nitrogen and sulphur are generally in the range 1 ppm to 100 ppm by weight approximately, preferably less than 100 ppm, depending on their nature. They may be up to 1% by weight for particular feeds.

The treated feed may advantageously be unrefined, or it may have undergone a refining or pre-refining treatment the aim of which is to reduce the quantity of metals. This pre-treatment step may have been carried out in advance, or in a pre-treatment section placed upflow of the hydrotreatment reactor. This optional pre-treatment step advantageously consists of a heat treatment associated with passage over solids such as aluminas or silica-aluminas, or a treatment with steam or a treatment with acid such as phosphoric acid, for example, or a treatment with an ion exchange resin, or indeed a combination of several of these pre-treatment steps. In general, the pre-treatment may include any of the methods (degumming, dephosphatation, etc.) known to the skilled person dealing with refining food quality oil.

The invention will now be described with reference to the figures to facilitate comprehension; the figures do not limit the general nature of the invention.

Hydrotreatment

The feed, also termed the fresh feed, is injected into the line 1 represented in FIG. 1. This feed is mixed with a hydrogen-rich gas 2, but it may also contain other inert hydrocarbon compounds, i.e. which do not react per se with the constituents of the feed. The hydrogen may advantageously be derived from a makeup of hydrogen and/or from recycling hydrogen-rich gas obtained from the separation step after the hydrotreatment step. In practice, the makeup hydrogen may be derived from steam reforming or from catalytic reforming, and its purity is usually in the range 75% to 95% by volume of hydrogen, the other gases present generally being methane, ethane, propane and butane. The hydrogen-rich gas obtained from the separation step after the hydrotreatment step preferably undergoes one or more intermediate purification treatments before being recycled to the hydrotreatment process.

Figure 2:
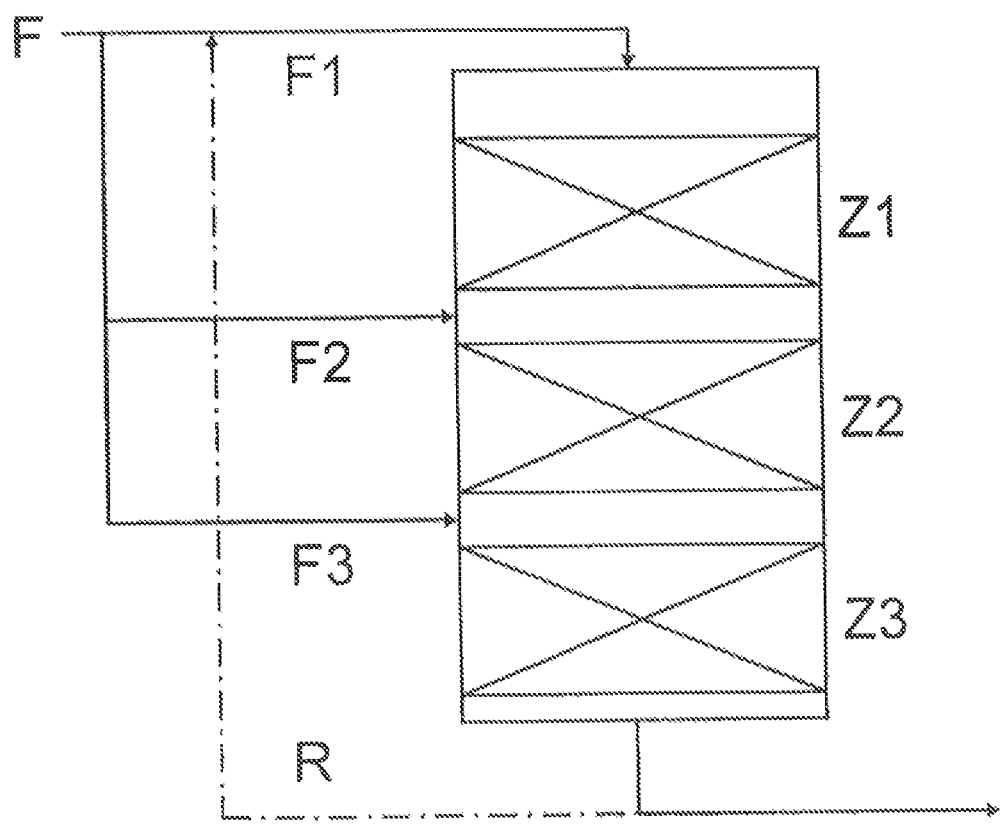
FIG. 2 represents a reactor in accordance with the invention.

In accordance with one feature of the invention, the hydrogen used is in excess with respect to the theoretical consumption, the excess hydrogen representing at least 50% of this theoretical consumption, preferably in the range 75% to 400%, and still more preferably in the range 100% to 300%, 150% being a typical value. The quantity of hydrogen employed is controlled by the partial pressure of the hydrogen For ease of comprehension of the present invention, the following definitions will be introduced. They refer to FIG. 2. The reactor comprises n catalytic zones. All of the flows are expressed as a mass flow rate.

F: total flow of renewable feed treated in the process;

F1: part flow of feed introduced into the first catalytic zone Z1;

F2: part flow of feed introduced into the second catalytic zone Z2;

F3: part flow of feed introduced into the third catalytic zone Z3; and so on . . . .

Fn: part flow of feed introduced into the last catalytic zone Zn;

R: recycle flow, recycled to the first catalytic zone Z1.

The total recycle RT is defined as the ratio by weight between the recycle flow sent to the first catalytic zone Z1, R, and the total flow of the renewable feed, F:

$$RT = R/F$$

The local recycle, RF1, for the first catalytic zone is defined as the ratio by weight between the recycle flow sent to the first catalytic zone Z1, R, and the part flow of the feed introduced into the first catalytic zone 1, F:

$$RF1 = R/F1$$

Except for during the start-up phase of the process, the diluent which is recycled to the catalytic zone Z1, and thus upflow of the first catalytic bed, is constituted by a portion of the liquid hydrocarbon produced and constituted by linear paraffins, leaving the hydrotreatment section. This diluent agent recycled to the inlet to the first catalytic zone is also known as the liquid recycle or recycle in the remainder of this description, and its flow rate is denoted R in the definitions above. The hydrotreatment section of the process is designed so as to completely convert the treated feeds, and so the liquid recycle produced is a hydrocarbon flow which is free of oxygen, which means that its oxygen content is less than the analytical detection limit and is essentially composed of paraffins. As a consequence, this liquid recycle is inert as regards hydrotreatment reactions and thus acts as a diluent for the feed, which means that, due to the exothermic nature of the reactions occurring therein, the rise in temperature in the first catalytic zone can be limited. Nevertheless, for a given capacity, i.e. for a given mass flow rate of treated feed, denoted F, the aim is to limit the quantity of liquid recycle injected into the first zone, denoted R, and thus to limit the total flow rate of the flow supplying this catalytic zone. This means that it is possible to use hydrotreatment reactors with dimensions comparable to those of the hydrotreatment reactors of oil cuts such as gas oils (and thus to limit costs), to limit the pressure drops and to avoid choking phenomena in the reactor.

In practice, in accordance with a preferred feature of the invention, the weight ratio between the recycle flow sent to the first catalytic zone Z1 (denoted R) and the total flow of the treated renewable feed (denoted F), also termed the total recycle, RT, is preferably less than 1.0, and more preferably less than 0.5, said flows being expressed as the mass flow rate.

In accordance with the invention, the part feed flows are introduced into the various catalytic zones (F1 injected into zone Z1, F2 into zone Z2, etc.) such that increasing proportions of feed are injected into successive catalytic zones. Thus, in accordance with the invention, F1/F is less than or equal to F2/F, which itself is less than or equal to F3/F, etc. More generally, F(n−1)/F is less than or equal to Fn/F for the general case in which n is the number of catalytic zones employed.

The advantage provided by such a distribution of the feed in the various successive catalytic zones is based on the fact that the outlet temperatures from the various zones follow a rising profile, which means that at the outlet from each catalytic zone, sufficient temperatures can be obtained to completely eliminate oxygen and thus to produce an effluent containing at least hydrocarbon compounds constituted by linear paraffins.

In accordance with the invention, the temperature of the flow injected into the inlet to the first catalytic zone Z1, comprising and preferably constituted by the part flow of the feed F1 mixed with the hydrogen-rich gas H1 entering the zone Z1 and the liquid recycle R constituted by a portion of the liquid fraction of hydrocarbons constituted by linear paraffins, is greater than 250° C., preferably greater than 260° C. and more preferably greater than 270° C., and the temperature of the flows at the inlet to the subsequent catalytic zones Z2 to Zn is greater than 300° C., preferably greater than 310° C. and preferably greater than 320° C.

The flow at the inlet to the catalytic zones following the first zone and in particular the flow at the inlet to the second catalytic zone comprises:

the part flow of feed introduced into the second catalytic zone Z2, F2, such that the weight ratio F2/F is greater than the weight ratio F1/F;

the liquid recycle injected into the inlet to zone Z1, composed exclusively of linear paraffinic hydrocarbons having passed through zone Z1;

the flow of hydrogen-rich gas H2 entering Z2;

the effluent formed by conversion of the feed in the zone Z1, corresponding to the flow rate F1. The liquid hydrocarbons present in this effluent are oxygen-free and exclusively linear paraffinic hydrocarbons.

And so on for all of the catalytic zones following the first zone.

The temperature at the outlet from at least one catalytic zone is preferably greater than 320° C., more preferably greater than 350° C. The temperatures at the outlet from each of the catalytic zones must preferably be less than 400° C., so as to limit deactivation of the catalyst by coking.

In accordance with the invention, a part flow of feed F1 is injected into the first catalytic zone such that the weight ratio between the flow of liquid recycle, R, injected into the inlet to the first catalytic zone Z1 and the part flow of feed injected into the inlet to zone 1, F1, is 8 or more and preferably 10 or more, said flows being expressed as the mass flow rate. This ratio is also termed the local recycle.

The use of an arrangement of this type for the feed and liquid recycle flows combined with the inlet temperatures for the flows into the various specific catalytic zones means that:
  on the one hand, a homogeneous temperature can be obtained in the entire section of the reactor at the outlet from zone Z1;
  on the other hand, a sufficient temperature can be reached at the outlet from zone Z1 which can initiate decarboxylation reactions and thus maximize the proportion of linear paraffins containing at most 17 carbon atoms in the liquid hydrocarbon produced at the outlet from zone Z1, in the case in which the initial feed comprises compounds containing more than 17 carbon atoms;
  higher temperatures can be obtained at the outlet from the catalytic zones following zone Z1 (zones Z2 to Zn) which are sufficient to increase the relative importance of the decarboxylation reactions over the deoxygenation reactions.

In fact, introducing the feed in increasing proportions coupled with a substantial recycle to the first zone and the temperatures of the flows at the inlet to the various specific hydrotreatment catalytic zones means that, by means of a rising temperature profile, a sufficiently hot zone can be obtained at the end of the catalytic zone to favour decarboxylation reactions over hydrodeoxygenation reactions.

The local recycle ratio of 8 or more means that relatively little feed is injected into the first zone, thus meaning that the remainder of the feed can be injected into the successive catalytic zones in larger and increasing proportions. Increasing the quantity of the feed injected into the successive zones means that a rising profile of inlet and outlet temperatures can be obtained at the various zones.

During the start-up phases, a wide range of hydrocarbons can be injected until a sufficient quantity of paraffinic product is available for recycling to the inlet to zone Z1.

The feed is supplied via the line 1, as can be seen in FIG. 1, while the hydrogen-rich gas is supplied via line 2. The feed is distributed into the various flows F1, F2, . . . Fn supplying the various successive catalytic zones. The hydrogen-rich gas is distributed as flows H1, H2, . . . , Hn. The flow of feed F1 is mixed with the gas flow H1, the flow of feed F2 is mixed with the gas flow H2 and so on up to the $n^{th}$ catalytic zone.

The temperature of the feed flows F1, F2, . . . Fn is less than 150° C., preferably less than 100° C., and more preferably less than 80° C. It must be sufficient to allow a reduction in the viscosity which is sufficient and thus adequate transfer from the storage tanks to the hydrotreatment reaction section. It is neither useful nor desirable to raise the temperature of the feed to higher values in the absence of hydrogen in order to avoid any degradation of the feeds as a result of polymerization and coking, for example.

The temperature of the hydrogen-rich gas which is mixed with the feed may be adjusted in order to contribute to obtaining the desired temperature of the flows at the inlet to the various catalytic zones.

In practice, since the temperature rises during compression of the hydrogen-rich gas, the hydrogen is optionally cooled after compression. Usually, the temperature of the hydrogen-rich gas is in the range 40° C. to 100° C., for example 50° C.

Introduction of the feed in increasing proportions coupled with a substantial recycle to the first zone and temperatures of the flows at the inlet to the various specific catalytic hydrotreatment zones must be carefully regulated so as to allow all of the reactions to initiate, in particular the decarboxylation/decarbonylation reactions resulting in the formation of $CO_2$ and CO. The temperatures of the flows at the inlet to the various catalytic zones may be adjusted as a function of the nature of the feed. The volume of the catalyst used in this catalytic zone is adapted such that the conversion—i.e. the degree of oxygen elimination—is complete at the outlet from this zone Z1.

At the outlet from the catalytic zone Z1, the second flow of feed F2 is added, which represents a higher proportion of feed than that injected into the inlet to zone Z1. This feed injected into the inlet to zone Z2 may be strictly identical to that injected into the inlet to zone Z1, but also may be a feed of renewable origin but with a different nature. This flow of feed is supplemented with hydrogen-rich gas flow (H2) and it is injected in its entirety into the reaction zone where it is mixed with the effluent from zone Z1. This allows the temperature of the product formed at the end of zone Z1 to be reduced and the temperature at the inlet to zone Z2 is thus generally higher than that at the inlet to zone Z1 and must be adjusted to a temperature of more than 300° C. in accordance with the invention. The same families of reactions occur in zone Z2 and in zone Z1 with slightly faster kinetics in zone Z2 due to a higher mean temperature.

The same principle then applies in the successive catalytic zones, the flow of feed being supplemented with completely converted product formed in the subsequent catalytic zones.

As the feed is transformed into linear paraffinic hydrocarbons in one catalytic zone, the temperature increases in the zone, since hydrogenation and decarboxylation reactions are highly exothermic.

The ratios between the flow rates of hydrogen added to each of these flows F1, . . . Fn and the mass flow rates of feed F1, . . . Fn are of the same order of magnitude for all of the catalytic zones, the ratio between the flow rate of hydrogen and the flow of feed rate being in the range 300 to 1500 $Nm^3/m^3$, preferably in the range 600 to 900 $Nm^3/m^3$.

Optionally, it is possible to inject a complementary flow of liquid between the catalytic zones if further dilution of the feed is deemed necessary.

In accordance with a preferred variation, valves for regulating the part flows of feed and hydrogen may be controlled by the temperatures at the inlets and outlets for the catalytic zones so as to adjust the part flows of feed and hydrogen as well as the flow of liquid recycle during operation. In this manner, the desired temperature at the inlet to the catalytic zones and in the catalytic zones is maintained. This is illustrated by the dotted lines in FIG. 1. Similarly, the temperature may be controlled by varying the temperature of the feed and/or the hydrogen injected and/or the recycle (via the exchanger 14) in the reactor system (see above).

The hydrotreatment reactor of step a) of the process of the invention may contain a variable number of catalytic zones. It usually comprises in the range 3 to 10 catalytic zones, preferably in the range 3 to 6 catalytic zones. The term "catalytic zone" means a catalytic bed. Each catalytic zone may comprise one or more layers of catalyst, identical or different, optionally supplemented by inert layers. The catalytic zones may contain identical or different catalysts.

In accordance with the invention, the hydrotreatment step a) is operated in the presence of a hydrotreatment catalyst. The type of catalyst used in the hydrotreatment step a) of this process is well known in the art.

Preferably, the catalyst used in the hydrotreatment step a) does not comprise zeolite.

The catalysts used in the hydrotreatment section of the process of the invention may be a combination of the catalysts described below.

The catalyst used in said step a) may advantageously be in the supported or bulk form.

The catalyst used in said step a) may advantageously be in the metallic or sulphide form.

In the case in which said catalyst is a supported catalyst, said hydrotreatment catalyst advantageously comprises one or more elements from groups 6, 8, 9 and 10 of the periodic classification of the elements, preferably selected from nickel, molybdenum, tungsten and/or cobalt, used alone or as a mixture, and a support selected from the group formed by alumina, silica, silica-aluminas, magnesia, clays and mixtures of at least two of these minerals. This support may also advantageously comprise other compounds, for example oxides selected from the group formed by boron oxide, zirconia, titanium oxide and phosphoric anhydride. The preferred support is an alumina support, highly preferably η, δ or γ alumina.

The quantity of oxides of metals from group 8 is advantageously in the range 0.5% to 10% by weight of oxide, preferably in the range 1% to 5% by weight of oxide, and the quantity of oxides of metals from group 6 is advantageously in the range 1% to 30% by weight of oxide, preferably 5% to 25% by weight, the percentages being expressed as a % by weight with respect to the total catalyst mass.

The total quantity of oxides of metals from groups 6 and 8 in the catalyst used is advantageously in the range 5% to 40% by weight and preferably in the range 6% to 30% by weight with respect to the total catalyst mass.

The weight ratio, expressed as the metal oxide, between the metal (or metals) from group 6 and the metal (or metals) from group 8 is advantageously in the range 20 to 1, preferably in the range 10 to 2.

Said catalyst used in the hydrotreatment step of the process of the invention may also advantageously contain a doping element selected from phosphorus and boron, used alone or as a mixture. Said doping element may be introduced into the matrix or, as is preferable, deposited on the support. It is also possible to deposit silicon on the support, alone or with the phosphorus and/or boron and/or fluorine.

The quantity by weight of the oxide of said doping element is advantageously less than 20% and preferably less than 10% and it is advantageously at least 0.001% with respect to the total catalyst mass.

In the case in which said catalyst is in the sulphide form, a sulphur-containing compound such as dimethyldisulphide (DMDS) is advantageously added to the set of feed flows. Under the temperature conditions of hydrotreatment step a), said compound decomposes into $H_2S$ and methane. This device can be used to keep the hydrotreatment catalysts used in the present process in their sulphide form, and thus to maintain a sufficient catalytic activity throughout the cycle. The quantities of DMDS injected which are recommended are in the range 10 to 50 ppm by weight of sulphur equivalent with respect to the feed. In practice, adding DMDS corresponding to 50 ppm by weight of sulphur equivalent with respect to the feed is sufficient to retain the catalytic activity throughout the cycle.

In the case in which said catalyst is in the metallic form, said catalyst advantageously comprises a metal selected from nickel, platinum, palladium, ruthenium and rhodium, supported on a support selected from alumina, silica, silica-alumina, carbon, activated carbon, cerine and zirconia or a mixture of these compounds.

A preferred metallic catalyst comprises 0.05% to 10% by weight, preferably 0.1% to 5% by weight of at least one noble metal from group VIII, preferably selected from platinum and palladium; more preferably, said noble metal is platinum deposited on a support.

Another preferred metallic catalyst comprises 5% to 75% by weight of a non-noble metal from group VIII, preferably nickel, deposited on a support.

The context of the present invention includes using a single catalyst or several different catalysts, simultaneously or successively, in the catalytic zones in hydrotreatment step a) of the process of the invention.

The hydrotreatment step a) of the process of the invention thus means that, by means of the combination of conditions employed and explained above, deoxygenation in the decarboxylation/decarbonylation pathway is favoured. The effluent containing at least the hydrocarbon compounds constituted by linear paraffins obtained from step a) thus primarily comprises odd-numbered linear paraffinic hydrocarbon compounds rather than even-numbered hydrocarbon compounds.

The selectivity for the decarboxylation/decarbonylation pathway is demonstrated by measuring the total yield of hydrocarbons with an odd number of carbon atoms and the total yield of hydrocarbons with an even number of carbon atoms in the linear liquid paraffinic hydrocarbon fraction. The yields of odd-numbered and even-numbered hydrocarbons providing access to the selectivity of the reaction (decarbonylation/decarboxylation/HDO) are obtained by gas phase chromatographic analysis of the liquid effluents obtained in step a). The gas phase chromatographic analysis measurement technique is a method which is familiar to the skilled person.

Unless otherwise indicated, the process of the invention is operated under hydrotreatment conditions which are generally known in the art such as, for example in patent EP 1 741 768. The total pressure is generally in the range 20 to 150 bar (2 MPa to 15 MPa), preferably in the range 50 to 100 bar (5 MPa to 10 MPa).

As indicated above, the hydrogen is used in excess. In the process of the invention, the ratio between the hydrogen flow rate and the unrefined flow of feed rate is in the range 300 to 1500 $Nm^3/m^3$, preferably in the range 600 to 900 $Nm^3/m^3$.

A satisfactory operation of the process of the invention results in using an overall HSV (defined as the ratio between the total volume flow rate of unrefined treated feed and the total volume of catalyst in the hydrotreatment section) in the range 0.1 to 50 $h^{-1}$, preferably in the range 0.1 to 1.5 $h^{-1}$.

The temperatures used in the various zones of the hydrotreatment section must be carefully controlled in order to avoid, as far as possible, unwanted reactions such as polymerization reactions of the feed, leading to the deposition of coke and thus to deactivation of the catalyst, while carrying out total conversion of the feed, i.e. completely eliminating the oxygen-containing compounds, preferably by decarboxylation/decarbonylation. In general, the process of the invention is operated at a temperature in the range 200° C. to 400° C.

The process of the invention uses fixed trickle bed reactors which are known to the skilled person. The reagents (feed and hydrogen) are introduced into the reactor which is in co-current downflow mode, with a flow from top to bottom of the reactor. Reactors of this type are described in the document U.S. Pat. No. 7,070,745, for example.

Between each catalytic zone, it is possible to inject supplemental hydrogen in order to benefit from a quench effect and to obtain the desired temperatures at the inlet to the next catalytic zone. Thus, quench boxes may be installed between each catalytic zone in order to provide better homogeneity of the temperatures over the entire section of the reactor and for all of the catalytic zones.

In the same manner, distributors could be installed between each catalytic zone in order to ensure a homogeneous supply of liquid feed over the whole section of the reactor and for all the catalytic zones.

One advantage of the process of the invention consists in its great flexibility, depending on the origin of the feed. Feeds which differ substantially from each other, in particular by having different levels of unsaturation of the hydrocarbon chains, can be completely converted as regards elimination of oxygen (which results in maximum efficiency of dilution of the unrefined feed in the next zone).

Separation

In accordance with the invention, the effluent containing at least hydrocarbon compounds constituted by linear paraffins formed in the last catalytic zone obtained from step a) is withdrawn in the line 11 and then undergoes at least one separation step in order to separate a gaseous fraction containing hydrogen, CO, $CO_2$, $H_2S$, water and light gases and a liquid hydrocarbon fraction constituted by linear paraffins.

In a variation, the separation may be carried out in a single step using a high temperature, high pressure separator 8 operating without reduction of pressure at a temperature in the range 145° C. to 280° C.

In another variation, the separation step comprises separating in two steps without reduction of pressure, the first separation being carried out between 145° C. and 280° C. in a high temperature separator 8, the second being carried out between 25° C. and 100° C. in a low temperature separator 9. In a preferred embodiment, the condensate from the fraction obtained from the second separation step is introduced into a degassing vessel 12.

Preferably, the liquid effluent obtained from the preceding gas/liquid separation then undergoes separation (not shown in the figure) of at least a portion, preferably all of the remaining quantity of the water formed, from at least one liquid hydrocarbon base, the water being produced during the hydrodeoxygenation reactions.

The aim of this step is to separate the water from the liquid hydrocarbon effluent. The term "water elimination" means elimination of the water produced by the hydrodeoxygenation reactions (HDO).

The water may be eliminated using any of the methods and techniques known to the skilled person such as, for example, by drying, by passage over a dessicant, by flash, by solvent extraction, distillation and decantation or by combining at least two of these methods.

Optionally, a step for final purification of the various pollutants may be carried out using methods which are known to the skilled person such as, for example, by steam or nitrogen stripping or by coalescence and/or a capture mass.

In accordance with the invention, at least a portion of the liquid hydrocarbon fraction constituted by linear paraffins obtained from the separation step is recycled to the first catalytic zone Z1 in a manner such that the weight ratio between the flow for said recycle and the part flow F1 introduced into the first catalytic zone Z1 is greater than 8, preferably greater than 10.

The portion of the liquid hydrocarbon fraction constituted by linear paraffins obtained from the separation step 10 which is not recycled to supplement the flow of feed injected into the zone Z1 as a liquid recycle R may advantageously be sent to an optional fractionation section 15 in order to separate a liquid hydrocarbon fraction via the line 16 constituted by linear paraffins containing at most 17 carbon atoms (C17− fraction) and a liquid hydrocarbon fraction constituted by linear paraffins containing 18 carbon atoms or more (C18+) via the line 18.

In a variation, only the linear paraffins containing at most 17 carbon atoms are sent to the transformation step b) (zone 16) of the process of the invention.

The hydrogen-containing gas 13 which has been separated during the separation step ii) of the process of the invention is advantageously, if necessary, at least partially treated to reduce its light compounds content ($C_1$ to $C_4$). Similarly, it advantageously undergoes one or more intermediate purification treatments, preferably at least one wash with at least one amine, preferably followed by methanation and/or separation by pressure swing adsorption (PSA), before being recycled.

Recycle hydrogen may advantageously be introduced, preferably purified, either with the feed entering the hydrotreatment step a) of the invention or in the form of quench hydrogen between the beds of hydrotreatment catalysts in the invention.

Transformation into Surfactant Compounds

In accordance with the invention, at least a portion of said liquid hydrocarbon fraction constituted by linear paraffins 10 obtained from step a), and preferably a liquid hydrocarbon fraction constituted by linear paraffins containing at most 17 carbon atoms (C17− fraction) is sent to a step b) for transformation into surfactant compounds. The step b) for transformation into surfactant compounds takes place in a zone 15.

Preferably, said step b) is:

either a step for alkylation of at least a portion of said liquid hydrocarbon fraction constituted by linear paraffins obtained from step a), and preferably a liquid hydrocarbon fraction constituted by linear paraffins containing at most 17 carbon atoms (C17− fraction), by aromatic hydrocarbons selected from benzene, toluene, xylenes or mixtures of these hydrocarbons, in order to produce aromatic compounds alkylated by long chain paraffins;

or a step for sulphonation of at least a portion of said liquid hydrocarbon fraction constituted by linear paraffins obtained from step a), preferably a liquid hydrocarbon fraction constituted by linear paraffins containing at most 17 carbon atoms (C17− fraction), in order to produce paraffinic sulphonate compounds.

The paraffinic sulphonates, like the aromatics alkylated by long chain paraffin chains, have surfactant properties which allow them to be used as detergent bases.

Alkylation

In the case in which said step b) is an alkylation step, said alkylation step is carried out in the presence of an alkylation catalyst selected from aluminium chloride and hydrofluoric acid, alone or in combination with zeolites. The alkylation catalysts are catalysts which are known in the art. In said alkylation step, at least a portion of said liquid hydrocarbon fraction constituted by linear paraffins obtained from step a), preferably a liquid hydrocarbon fraction constituted by linear paraffins containing at most 17 carbon atoms (C17− fraction), is brought into contact with aromatic hydrocarbons selected from benzene, toluene, xylenes and mixtures of these compounds.

The alkylation reaction may be carried out by homogeneous catalysis or by heterogeneous catalysis, as indicated in application US 2011275871A.

Upflow of this alkylation step, at least a portion of said liquid hydrocarbon fraction constituted by linear paraffins obtained from step a), preferably a liquid hydrocarbon fraction constituted by linear paraffins containing at most 17 carbon atoms (C17− fraction) preferably undergoes a dehydrogenation step in order to produce linear mono-olefinic compounds. This step is particularly important.

The principal features of the dehydrogenation reaction are that the thermodynamic equilibrium limits the level of conversion per pass and that the reaction is highly endothermic. Thus, the step for dehydrogenation of the n-paraffins is preferably carried out at temperatures of more than 400° C. with a degree of conversion per pass in the range 10% to 25%, limited by the thermodynamics. Preferably, the dehydrogenation step is carried out in hydrogen with a H2/feed molar ratio in the range 0.5 to 10, the temperature being in the range 400° C. to 800° C., the total pressure being in the range 0.01 to 2 MPa, the hourly space velocity being in the range 0.5 to 300 h$^{-1}$.

The catalysts for dehydrogenation of the n-paraffins which are known to the skilled person are multimetallic: they generally contain platinum, tin and indium. The presence of acidity on the support favours unwanted cracking and isomerization reactions to form unwanted products.

The effluent obtained from the optional dehydrogenation step is then brought into contact with aromatic hydrocarbons selected from benzene, toluene, xylenes and mixtures of these compounds.

In the case in which said alkylation reaction is carried out by homogeneous catalysis, an acidic liquid catalyst is used such as hydrofluoric acid, HF, or sulphuric acid, $H_2SO_4$. The temperature is in the range 10° C. to 80° C., preferably in the range 20° C. to 60° C., and more preferably in the range 30° C. to 50° C. The pressure is in the range 0.2 to 4 MPa, preferably in the range 0.2 to 3 MPa. The volumetric ratio between the acid and the olefin+paraffin hydrocarbon flow to be converted is in the range 0.1 to 10 vol/vol, preferably in the range 1 to 3 vol/vol. The molar ratio between the aromatic hydrocarbon flows and the paraffinic hydrocarbon flow is in the range 1 to 15 mol/mol, preferably in the range 5 to 12 mol/mol. The contact time is in the range 5 to 50 min, preferably in the range 20 to 40 min.

In the case in which said alkylation reaction is carried out by heterogeneous catalysis, a solid amorphous or zeolitic acid catalyst is used selected from silica-alumina, fluorinated silica-alumina, zeolites of the FAU, MOR, MTW, OFF, MAZ, BEA or EUO type, or mixtures of these solids. The zeolites contain an element X selected from Si or Ge, and an element T selected from Al, Fe, Ga and B.

The temperature is in the range 30° C. to 400° C., preferably in the range 50° C. to 300° C., and still more preferably in the range 70° C. to 300° C. The pressure is in the range 0.1 to 10 MPa, preferably in the range 1 to 7 MPa. The hourly space velocity or HSV is in the range 0.01 to 200 h$^{-1}$, preferably in the range 0.5 to 80 h$^{-1}$. It may be carried out in a fixed bed or a moving bed. The molar ratio between the flow of aromatic hydrocarbons and the paraffinic+olefinic hydrocarbons is in the range 2 to 50 mol/mol, preferably in the range 5 to 35 mol/mol.

The surfactant compounds formed at the end of this alkylation step are aromatic hydrocarbons alkylated by long linear paraffins such as linear alkyl benzenes, for example.

Sulphonation

In the case in which said step b) is a sulphonation step, at least a portion of said liquid hydrocarbon fraction constituted by linear paraffins obtained from step a), preferably a liquid hydrocarbon fraction constituted by linear paraffins containing at most 17 carbon atoms (C17− fraction) undergoes a treatment with an acid selected from sulphuric acid, chlorosulphonic acid, an oleum, sulphur trioxide, $SO_3$, and sulphurous anhydride, optionally in the presence of air. The heat released during this exothermic sulphonation reaction is eliminated by external cooling, the temperature of the reaction mixture advantageously being maintained at between 20° C. and 100° C.

Sulphonation is known to the skilled person.

Neutralization is then advantageously carried out using a salt containing elements selected from sodium, potassium, ammonium, magnesium and mixtures of these salts. Long chain paraffin sulphonate type compounds (also known as Linear Alkyl Sulphonates or LAS) are thus obtained, with general formula R—$SO_3$—X, where R is a hydrocarbon chain and X is a cation which may be sodium, potassium, ammonium or magnesium. These long chain paraffin sulphonates have surfactant properties which make their use advantageous for various applications (detergents, emulsifiers, solubilizing agents, foaming agents or dispersing agents, for example).

The invention claimed is:

1. A process for the production of surfactant compounds from a feed obtained from renewable sources, comprising an oil or fat of vegetable or animal origin, or mixtures thereof, said oil or fat containing triglycerides and/or free fatty acids and/or esters, said process comprising:
   a) hydrotreatment of said feed in the presence of hydrogen in excess of theoretical hydrogen consumption and under hydrotreatment conditions, in a fixed bed reactor having a plurality of catalytic zones disposed in series and comprising a hydrotreatment catalyst, in order to produce an effluent containing at least linear paraffin hydrocarbon compounds,
   i) dividing the total flow of feed F into a certain number of different part flows, F1 to Fn, equal to the number of catalytic zones Zn in the reactor, injecting the first part flow F1 into a first catalytic zone Z1, injecting a second part flow F2 into a second catalytic zone, if n is greater than 2, up to n, various part flows being injected into successive catalytic zones in increasing proportions such that F1/F is less than or equal to F2/F, which itself is less than or equal to F3/F if present until F(n−1)/F is less than or equal to Fn/F,
   the temperature of a flow injected into the inlet to the first catalytic zone Z1 comprising part flow of the feed F1 mixed with a hydrogen-rich flow H1 entering the zone Z1 and with a liquid recycle R, (F1+R+H1), being greater than 250° C. and the temperature of flows at the inlet to the subsequent zones Z2 to Zn being greater than 300° C.;
   ii) separating from said effluent containing linear paraffin hydrocarbon compounds, a gaseous fraction containing hydrogen, CO, $CO_2$, $H_2S$, water and light gases and a liquid hydrocarbon fraction containing linear paraffins;
   iii) recycling at least a portion R of said liquid hydrocarbon fraction containing linear paraffins is recycled to the first catalytic zone Z1 such that the weight ratio between flows of said recycle R and the part flow F1 introduced into the first catalytic zone Z1, R/F1, is 8 or more;
   b) transforming at least a portion of said liquid hydrocarbon fraction containing linear paraffins obtained from a) into surfactant compounds, by
   alkylating of at least a portion of said liquid hydrocarbon fraction containing linear paraffins obtained from a), with aromatic hydrocarbons that are benzene, toluene, xylenes or mixtures of these hydrocarbons, in order to produce aromatic compounds alkylated by long chain paraffins;
   or sulfonating of at least a portion of said liquid hydrocarbon fraction containing linear paraffins obtained from a) in order to produce paraffinic sulfonate compounds.

2. The process according to claim 1, in which the excess hydrogen used in the hydrotreatment step is at least 50% beyond theoretical consumption.

3. The process according to claim 1, in which the weight ratio between the recycle flow sent to the first catalytic zone and the total flow of feed is less than 1, preferably less than 0.5.

4. The process according to claim 1, in which the feed obtained from renewable sources is oil or fat of vegetable or animal origin, or mixtures thereof, containing triglycerides and/or free fatty acids and/or esters.

5. The process according to claim 1, in which the temperature of the flow F1 injected into the inlet to the first catalytic zone Z1 is greater than 260° C.

6. The process according to claim 5, in which the temperature of the flow F1 injected into the inlet to the first catalytic zone Z1 is greater than 270° C.

7. The process according to claim 1, in which the temperature of the flows at the inlet to the catalytic zones Z2 to Zn is greater than 310° C.

8. The process according to claim 1, in which the hydrotreatment is operated at a temperature in the range 200° C. to 400° C., a total pressure in the range 2 MPa to 15 MPa, at an hourly space velocity in the range $0.1\ h^{-1}$ to $5\ h^{-1}$ and in the presence of a total quantity of hydrogen mixed with the feed such that the hydrogen/feed ratio is in the range 300 to 1500 $Nm^3$ of hydrogen/$m^3$ of feed.

9. The process according to claim 1, in which the hydrotreatment catalyst is a sulfur containing catalyst comprising one or more elements from groups 6, 8, 9 and 10 of the periodic classification of the elements, used alone or as a mixture, and a support of alumina, silica, silica-aluminas, magnesia, clays or mixtures of at least two of these minerals.

10. The process according to claim 1, in which the hydrotreatment catalyst is a metallic catalyst which comprises nickel, platinum, palladium, ruthenium and rhodium, supported on a support that is alumina, silica, silica-alumina, carbon, activated carbon, cerine, zirconia or a mixture of these compounds.

11. The process according to claim 1, in which at least a portion of the liquid hydrocarbon fraction containing linear paraffins obtained from the separation (ii) is recycled to the first catalytic zone Z1 such that the weight ratio between the flow for said recycle and the part flow F1 introduced into the first catalytic zone Z1 is greater than or equal to 10.

12. The process according to claim 1, in which the portion of the liquid hydrocarbon fraction containing linear paraffins obtained from the separation (ii) which is not recycled to supplement the flow of feed injected into the zone Z1 as a liquid recycle (R) is sent to a fractionation section in order to separate a liquid hydrocarbon fraction constituted by linear paraffins containing at most 17 carbon atoms (C17− fraction) and a liquid hydrocarbon fraction constituted by linear paraffins containing 18 carbon atoms or more (C18+).

13. The process according to claim 12, in which only the linear paraffins containing at most 17 carbon atoms are sent to the step b) for transformation in accordance with the process of the invention.

14. The process according to claim 1, wherein the linear paraffins in (b) have at most 17 carbon atoms.

15. The process according to claim 9, wherein the catalyst contains nickel, molybdenum, tungsten, cobalt or a mixture thereof.

* * * * *